United States Patent
Greene et al.

(10) Patent No.: US 6,288,379 B1
(45) Date of Patent: Sep. 11, 2001

(54) USE OF CONTINUOUSLY VARIABLE POWER IN MICROWAVE ASSISTED CHEMISTRY

(75) Inventors: Gary Roger Greene, Waxhaw; David Allan Barclay, Charlotte, both of NC (US)

(73) Assignee: CEM Corporation, Matthews, NC (US)

(*) Notice: Subject to any disclaimer, the term of this patent is extended or adjusted under 35 U.S.C. 154(b) by 0 days.

(21) Appl. No.: 09/343,349

(22) Filed: Jun. 30, 1999

Related U.S. Application Data

(62) Division of application No. 09/063,545, filed on Apr. 21, 1998.

(51) Int. Cl.[7] .................................................. H05B 6/68
(52) U.S. Cl. .............................................. 219/702; 219/679
(58) Field of Search ................................ 219/702, 679, 219/710, 690, 753, 754, 601, 716, 712, 718, 750; 363/98, 132

(56) References Cited

U.S. PATENT DOCUMENTS

| | | |
|---|---|---|
| 3,868,602 | 2/1975 | Meddaugh . |
| 3,995,133 | 11/1976 | Anderson . |
| 4,001,537 | 1/1977 | Burke et al. . |
| 4,023,004 * | 5/1977 | Burke ................................. 219/718 |
| 4,041,267 | 8/1977 | Wechsler . |
| 4,149,057 | 4/1979 | Fritts . |
| 4,326,114 | 4/1982 | Gerling et al. . |
| 4,370,535 * | 1/1983 | Noda ................................... 219/712 |
| 4,481,447 | 11/1984 | Stupp et al. . |
| 4,506,127 * | 3/1985 | Satoh ................................. 219/710 |
| 4,517,430 | 5/1985 | Slottag . |
| 4,742,442 * | 5/1988 | Nilssen .............................. 363/98 |
| 4,816,986 | 3/1989 | Spiridonov et al. . |
| 4,825,028 * | 4/1989 | Smith ................................. 219/716 |
| 4,873,408 | 10/1989 | Smith et al. . |
| 4,900,884 * | 2/1990 | Aoki .................................. 219/601 |
| 4,900,885 | 2/1990 | Inumada . |
| 4,996,403 | 2/1991 | White . |
| 5,179,264 | 1/1993 | Cuomo et al. . |
| 5,191,182 | 3/1993 | Gelorme et al. . |
| 5,241,040 | 8/1993 | Cuomo et al. . |
| 5,264,185 | 11/1993 | Floyd . |
| 5,317,081 | 5/1994 | Gelorme et al. . |
| 5,317,133 | 5/1994 | Sundstrom et al. . |
| 5,340,914 | 8/1994 | Cuomo et al. . |
| 5,344,493 | 9/1994 | Jackson . |
| 5,371,668 | 12/1994 | Gurwicz et al. . |
| 5,387,397 | 2/1995 | Strauss et al. . |
| 5,440,104 | 8/1995 | Koch et al. . |
| 5,443,795 | 8/1995 | Revesz . |

(List continued on next page.)

Primary Examiner—Teresa Walberg
Assistant Examiner—Quang Van
(74) Attorney, Agent, or Firm—Summa & Allan, P.A.

(57) ABSTRACT

A method of microwave assisted chemistry is disclosed in which power can be supplied more continuously at preferred power levels to more precisely control or moderate a chemical reaction. The method comprises measuring the duty cycle required to maintain a measured selected parameter of a sample at a predetermined set point while the sample is being exposed to microwave radiation at a first predetermined power level; and moderating the duty cycle and the applied microwave power to increase the on time of the duty cycle while applying power at a second predetermined power level that is sufficient to maintain the sample at the set point using the moderated duty cycle. A corresponding device for microwave assisted chemistry is also disclosed and comprises a cavity for receiving a sample, a waveguide connected to the cavity, a source of microwave radiation connected to the waveguide, and a switching power supply for driving the source of microwave radiation.

27 Claims, 1 Drawing Sheet

U.S. PATENT DOCUMENTS

| | | |
|---|---|---|
| 5,451,302 | 9/1995 | Cha . |
| 5,495,209 | 2/1996 | Gerstenberg . |
| 5,512,736 * | 4/1996 | Kang et al. .......................... 219/750 |
| 5,521,360 | 5/1996 | Johnson et al. . |
| 5,525,782 | 6/1996 | Yoneno et al. . |
| 5,532,642 | 7/1996 | Butwell et al. . |
| 5,548,101 * | 8/1996 | Lee ....................................... 219/601 |
| 5,548,103 | 8/1996 | Morita . |
| 5,715,155 * | 2/1998 | Shahani et al. ..................... 363/132 |
| 5,796,080 | 8/1998 | Jennings et al. . |
| 6,084,226 * | 7/2000 | Greene et al. ...................... 219/718 |

\* cited by examiner

USE OF CONTINUOUSLY VARIABLE POWER IN MICROWAVE ASSISTED CHEMISTRY

This application is a division of Ser. No. 09/063,545 filed Apr. 21, 1998.

FIELD OF THE INVENTION

The present invention relates to the use of microwave energy to heat chemical reactions, and in particular relates to a method of using continuously variable power to drive reactions more successfully.

BACKGROUND OF THE INVENTION

The present invention relates to the use of microwaves to provide a heating source for chemical reactions. The technique is generally referred as "microwave assisted chemistry" and has found wide application in various chemical reactions such as digestion, extraction, drying, moisture analysis, Kjeldahl reactions, sample preparation for further analysis such as spectroscopy, and other techniques.

The nature of microwave radiation provides a number of advantages in conducting chemical reactions. First, in contrast to some conventional heating techniques in which a vessel is heated externally in order to in turn heat the reagents inside, microwave radiation heats the reagents directly and can be carried out—and indeed is desirably carried out—in vessels that are unaffected by microwave energy. Thus, microwave radiation tends to heat chemical samples very quickly. As a result, certain types of reactions that previously took hours can be carried out in minutes using microwave devices.

As a second advantage, because microwaves heat the reagents rather than their ambient surroundings, the effect of the microwaves is direct rather than indirect.

These same characteristics, however, can cause disadvantages in certain procedures. This is particularly true when combined with the typical techniques for generating the microwave themselves. Those familiar with microwave assisted chemistry devices will recognize that the typical microwave source is a half wave rectified power supply that operates at 50 or 60 cycles per second (hertz). In the U.S. 60 cycles is most common, while in most of the rest of the world, 50 cycles is common. Such devices, when operating at full power, provide that power in pulses. As would be expected, however, full power from a source having a certain power rating (e.g., 300 watts), may be satisfactory for a few chemical reactions, but is often too much power for other reactions, particularly those using small samples. Accordingly, some technique must be used to moderate the power that can be applied to particular chemical reactions.

In one technique, a "linear" power supply can be incorporated; i.e., one for which the source's power level is widely adjustable. Such systems, however, require circuitry that bleeds off the excess energy as heat. The systems are large and cumbersome, making them generally impractical for the bench top chemical applications that are used with microwave assisted chemistry. Some present commercial microwave assisted chemistry devices use one to three capacitors to moderate the amplitude of the rectified waves at one, two, or three levels. Nevertheless, incorporating enough capacitors to give a full range of wave amplitude would be highly impractical given the present technology and economics.

Accordingly, a more typical technique for moderating power is to use a single amplitude of power, while moderating the amount of time during which the power is applied in order to obtain a desired average (rather than continuous) power level. For example, if 100 watts of average power are desired from a 300-watt power supply, the power supply is pulsed for a fraction of time that corresponds to the fraction of power desired. Thus, obtaining 100 watts of average power from a 300-watt power supply requires pulsing the power supply "on" for one third of its normal cycle and then "off" for two thirds of its cycle. Because, for example, most power supplies for bench top microwave assisted chemistry devices use alternating current and provide microwaves at a 60 hertz frequency, the shortest time period during which a pulse of power can be on or off is $\frac{1}{60}$ of a second (0.0167 seconds). Thus to obtain 100 watts average power from a 300 watt supply, the typical technique applies 300 watts of power for one pulse period (0.0167 seconds), and then turns the power off for the next two pulse periods (a total of 0.0333 seconds). As a result, the average power over the three pulse periods is 100 watts.

It will be immediately recognized, however, that although the average power was 100 watts, in reality 300 watts were applied on an on-and-off basis for repeated short time periods. This application of full power, even for short time periods, has particular disadvantages. These become even more exaggerated when lower average powers are required. For example, when a 5-watt average power is desired or required, it represents $\frac{1}{60}$ of the rated 300-watt power supply. Accordingly, the power supply would be pulsed on for one cycle and then off for 59 cycles to produce an average power of 5 watts; e.g., 300 watts divided by 60 time periods. It will thus be recognized that no time period existed in which 5 watts were applied, but instead 300 watts were applied for a very short period of time.

Applying high power for short time periods to create an average power offers significant disadvantages in certain circumstances. First, as noted above, microwaves apply energy directly to the sample and thus the results are often immediate rather that gradual or gentle. Thus, in a reaction where a small amount of power is required, the application of high power, even for a very short time period, can push the reaction past the desired point. In particular, the high power can supply enough energy to drive a reaction past the activation energy for an undesired associated reaction. As one example, the Kjeldahl technique is often used to determine the amount of nitrogen in a sample by converting the nitrogen to ammonia (in several steps) and then measuring the amount of ammonia. If too much microwave power is applied, however, the nitrogen can be overoxidized to an oxidation state that doesn't properly convert to ammonia, and the measured amount of ammonia does not properly reflect the amount of nitrogen that was originally present in the sample.

Additionally, the application of full power pulses to obtain average power can cause localized overheating. Although this does not represent a problem in some reactions, it can raise significant problems in others. In turn, other parameters, such as pressure, can be driven beyond the desired parameters for a particular reaction.

As another disadvantage, microwaves aren't always uniformly absorbed by liquid reagents. The non-uniformity of their absorption can accordingly give a discontinuous or non-representative reading to the control vessels frequently used in microwave systems.

Furthermore, the use of pulses in the conventional sense can preclude the use of microwave chemistry with certain sensitive or more sophisticated reactions that could otherwise be carried out with microwave assistance.

As another disadvantage, microwave assisted chemistry is often carried out simultaneously on a plurality of vessels in a single cavity. The vessels typically rotate on a turntable in an attempt to get the microwaves to distribute evenly among the reagents. The turntable, however, does not guarantee uniform distribution of microwave energy throughout a cavity. Furthermore, the presence of the samples, as well as the changes they undergo during microwave assisted chemistry, also change the energy distribution in the cavity.

Those familiar with microwave assisted chemistry techniques recognize that the microwaves are typically generated by a magnetron, and then are carried through a wave guide to the point at which they enter the cavity (sometimes referred as the "launcher"). In typical systems, the turntable rotates at a relatively moderate speed, for example about every 7 seconds. As noted above, if a relatively low average power (e.g., 5 or 10 watts) is desired from a typical power supply of about 300 watts, the microwaves are pulsed on for only about 16 milliseconds out of every second. When combined with the uncertain wave distribution among the vessels and samples in the cavity, the result can be a surprisingly wide power variation from sample to sample, with an associated wide variation in the progress and results of the intended chemical reactions. These uneven results are often further exacerbated because in typical systems only one vessel is used to give feedback (because of the complexity of measuring feedback for every vessel). Thus, the power is uniformly pulsed for all of the vessels based solely upon indications from the control vessel.

The net effect is that the pulsed power tends to be "off" much more than has been previously recognized. In exaggerated terms, the control vessel is being "smashed" with large amount of power for short periods of time, which is then turned off for relatively long periods of time. As a result, the reactions in the remaining unmonitored vessels may be experiencing quite different conditions, or reaching quite different stages of progress or completion, than the sample vessel.

As an additional problem, the power needed to heat a sample to a particular temperature is generally much greater than the energy required to maintain it at such temperature for a desired period of time while the reaction continues.

Accordingly, the need exists for a technique and apparatus for carrying out microwave assisted chemical reactions that avoids the undesired effects of applying large amounts of power for short periods of time in an attempt to obtain an average power, and an associated need likewise exists for a technique for concurrently heating multiple vessels that avoids the pitfalls associated with attempting to control the application of larger pulsed microwave power to multiple vessels using a single control vessel on intermittent basis.

OBJECT AND SUMMARY OF THE INVENTION

Accordingly, it is an object of the invention to provide a method and apparatus that provides a wider range of available power levels and more continuous application of those power levels than is presently available in devices suitable for benchtop laboratory techniques.

The invention meets these objects with a method of microwave assisted chemistry in which power can be supplied more continuously at preferred power levels to more precisely control or moderate a chemical reaction. The method comprises measuring the duty cycle required to maintain a measured selected parameter of a sample at a predetermined set point while the sample is being exposed to microwave radiation at a first predetermined power level, and moderating the duty cycle and the applied microwave power to increase the on time of the duty cycle while applying power at a second predetermined power level that is sufficient to maintain the sample at the set point using the moderated duty cycle.

In another aspect, the invention comprises a device for microwave assisted chemistry that includes a cavity (for receiving a sample), a waveguide connected to the cavity, a source of microwave radiation connected to the waveguide; and a switching power supply for driving the source of microwave radiation.

The foregoing and other objects and advantages of the invention and the manner in which the same are accomplished will become clearer based on the following detailed description taken in conjunction with the accompanying drawings in which:

DETAILED DESCRIPTION

Figure 1:
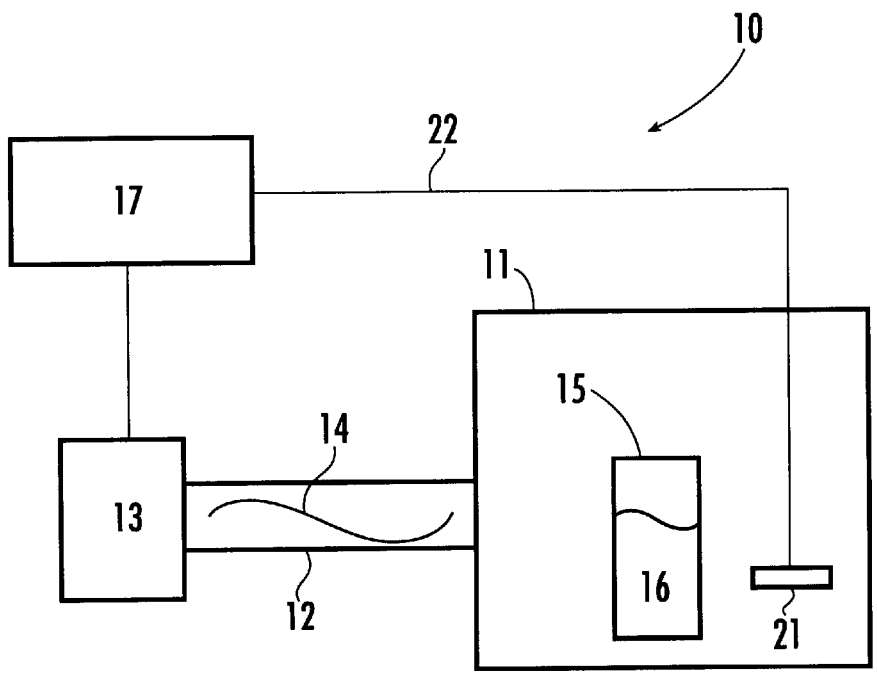
FIG. 1 is a schematic diagram of a microwave device according to the present invention and useful for practicing the present invention.

The invention is a method of microwave assisted chemistry in which power can be supplied more continuously at preferred power levels to more precisely control or moderate a chemical reaction. In this aspect, the invention comprises measuring the duty cycle required to maintain a measured selected parameter of a sample at a predetermined set point while the sample is being exposed to microwave radiation at a first predetermined power level. Thereafter, the duty cycle and the applied microwave power are moderated to increase the on time of the duty cycle while applying power at a second predetermined power level that is sufficient to maintain the sample at the set point using the moderated duty cycle. In an expanded sense, the method further comprises applying the first predetermined level of microwave power to the sample until the measured selected parameter reaches the predetermined set point and then cycling the power at the first predetermined power level to maintain the sample at the set point, both prior to the step of measuring the duty cycle.

There are a number of characteristics of chemical reactions that can be measured while microwave power is being applied to a sample. The most exemplary group includes temperature, pressure, pH, gas volume, liquid volume, color, and emission or absorption within the electromagnetic spectrum. It will be understood, however, that these are exemplary characteristics and that other characteristics can likewise be measured while still falling within the scope of the present invention.

As set forth in the background portion of the specification, the duty cycle of a microwave source is the repetitive fraction or percentage of time during which the source does or does not provide microwave power. For example, a simple duty cycle could consist of one second of applied microwave radiation followed by one second without any applied radiation. In most embodiments of the invention, the expectation and goal is to increase the amount of time that microwave radiation is being supplied while reducing the amount of power being supplied. Stated differently, the goal is to maximize the "on" time of the duty cycle while minimizing the applied power level and maintaining control based on the desired or measured characteristic.

As a simple example related to the discussion in the Background, an average power of 100 watts can be achieved by applying 300 watts using a duty cycle in which full power is applied for one second followed by two seconds without power so that the average power supplied over the three-second interval is 100 watts. In accordance with the invention, the power level is preferably reduced to 200 watts, while the on time of the duty cycle is increased to 1 second on and 1 second off. The result is the same; an average power of 100 watts, but achieved with a longer "on" cycle at a lower power level. Such provides the desired control for chemical reactions while avoiding artificially high power levels during artificially long "on" portions of the average duty cycles.

It will be further understood as set forth in the background, that the duty cycle of most microwave devices is at least about 50 cycles per second, and 60 cycles in the U.S., so that instead a typical microwave device being on for 1 second and off for 1 second, it is more typically on for $\frac{1}{60}$th of a second and then off for $\frac{1}{60}$th of a second.

Accordingly, in preferred embodiments the method of moderating the duty cycle to increase the on time comprises changing the applied microwave power to a second predetermined level, or some other level that is one of a set of predetermined levels.

Because the object of the invention is to continue to approach the longest possible "on" portion of the duty cycle at the lowest possible power level, the invention further comprises cycling the power from the first predetermined level to the second (usually lower) predetermined power level, measuring the duty cycle required to maintain the sample at the setpoint at the second predetermined power level, and thereafter further moderating the duty cycle and the applied microwave power to further increase the "on" time of the duty cycle while applying power at a third (i.e., one of a set of) predetermined level that remains sufficient to maintain the sample at the setpoint using the further moderated duty cycle. Thus, as the method continues, the step of further moderating the duty cycle comprises adjusting the applied microwave power to a third predetermined level and then (if necessary) to successive other power levels and increased "on" times of the duty cycle, to maintain the desired duty cycle while maintaining the measured selected parameter at the desired setpoint.

In preferred embodiments, the setpoint is a selected temperature or pressure at which a chemical reaction is to be maintained. There are a number of instruments and techniques available for measuring temperature which typically include thermometers, thermocouples, and optical pyrometers. The operation of such devices and the manner in which they can be associated with various control and feedback circuits are well understood in the electronic arts and will not otherwise be repeated herein in detail.

Similarly, pressure can be monitored either directly or indirectly, with well-known and well-understood devices that can be selected and used by those of ordinary skill in the art and without undue experimentation.

The method of the invention is best carried out using a switching power supply and preferably a resonant inverter to drive the magnetron. In the most preferred embodiments the resonant inverter is of the type available from Nada Electronics Ltd., Tyne & Wear, England. Such an inverter, its circuitry, and its manner of operation are set forth in U.S. Pat. No. 5,371,668 to Gurwicz et al., for "Resonant Inverter," which is incorporated entirely herein by reference. As general background, a resonant inverter is a species of a more general type of device referred to as a switching power supply. Generally, devices that convert alternating current (ac) to direct current (dc) are referred to as converters, while those that convert direct current to alternating current are called inverters. A thorough discussion of such converters is set forth in Dorf, The Electrical Engineering Handbook, Second Edition Section 30.2, Power Conversion, at pages 770–779 and Section 30.3, Power Supplies at pages 779–797.

In this aspect of the invention, the method preferably comprises using the resonant inverter to drive the magnetron at relatively high frequencies; i.e., up to 250,000 hertz (Hz). As will be understood based upon the previous discussions herein, the higher frequency greatly shortens the time required to obtain an average power from the source. Thus, the resonant inverter provides a technique for directing the same average power to a sample, but without exposing the sample to momentary bursts of high power. Instead, the invention provides the opportunity to expose the sample to more extended applications of power at lower power levels.

The example of 5 watts of average power from a 300 watt source (i.e., requiring 1 pulse period "on" and 59 "off") is again illustrative. For example, a 25,000 Hz resonant inverter provides pulse periods of $\frac{1}{25,000}$ second; e.g. 0.00004 seconds. Accordingly, 60 of these time periods are completed in only 0.0024 seconds. As a result, the power is supplied for very short periods that have little or no undesired effects on many samples as compared to the $\frac{1}{60}$ second power pulses from conventional 60 Hz sources. Also, at the higher frequencies, smoothing of the anode current is easily obtained, limiting the height of the peak power at lower power levels.

Figure 2:
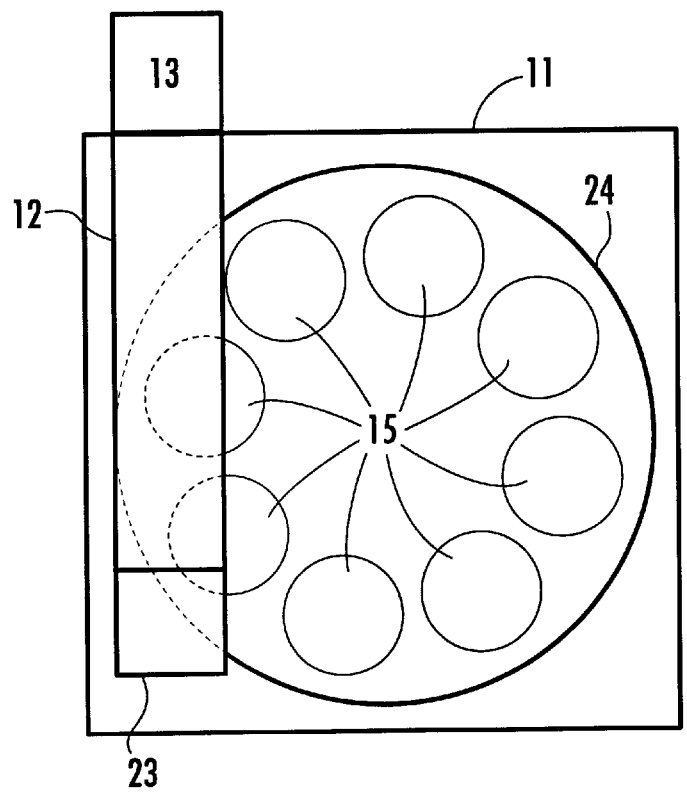
FIG. 2 is another schematic diagram of a device according to the present invention and similarly useful for practicing the present invention.

FIGS. 1 and 2 illustrate the apparatus aspects of the invention. FIG. 1 illustrates a device broadly designated at 10 for microwave assisted chemistry. The device 10 includes a cavity 11 which is connected to a waveguide 12 which in turn is connected to the microwave source 13. In preferred embodiments, the microwave source 13 comprises a magnetron. It will be understood that when used in relation to microwave transmission, the term "connected" means that microwaves, schematically indicated at 14, are desirably and properly transmitted through the waveguide 12 into the cavity 11. The cavity 11 is typically formed of a material (preferably metal or having a metal coating) that reflects microwaves and thus keeps the microwave energy in the cavity rather than allowing it to escape to the ambient surroundings. FIG. 1 also illustrates that in the preferred embodiment a reaction vessel 15 containing a sample 16 is present in the cavity for the purpose of having the sample heated (in most circumstances) by the applied microwave energy. A resonant inverter 17 drives the magnetron 13 to produce microwaves at the desired frequency and power level. The appropriate circuitry is set forth in the '688 patent incorporated earlier and are simply schematically designated at 20 in FIG. 1.

Depending upon the particular chemical reaction being carried out, the vessel 15 can be closed or open and may also be pressure resistant (if closed) if desired or necessary. In order to permit the microwave energy to desirably effect the sample 16, the vessel 15 is usually formed of a material that transmits (i.e., is substantially transparent to) microwave energy of the desired frequencies. It will be understood, of course, that in some circumstances the vessel is intended to absorb microwaves and change them to heat; i.e., to act as a susceptor.

A number of different types of reaction vessels are well known to those of ordinary skill in this art and are exemplified, but not limited to those available from CEM Corporation, the assignee of the present invention and that are described in several U.S. Patents and in the commercial and scientific literature. In most cases, in addition to being transparent to microwave radiation, the container should also be chemically inert with respect to the sample or reagents to be placed therein. Where necessary, the vessels are also pressure resistant, at least to the pressures normally expected to be generated by particular reaction, along with an appropriate safety margin.

It will be further understood in some circumstances, a plurality of reaction vessels are placed in a single cavity, while in other applications a single vessels is placed in a single respective cavity. One example (of many possible) of a device with a plurality of vessel in a single cavity is set forth in U.S. Pat. No. 5,320,804 which is commonly assigned with the present invention to CEM Corporation. An exemplary device in which individual reaction vessels are maintained in individual cavities is set forth in copending application Ser. No. 08/538,745, filed Oct. 3, 1995, by Jennings et al. for "Microwave Apparatus for Controlling Power Levels in Individual Multiple Cells," and now U.S. Pat. No. 5,796,080.

FIG. 1 also illustrates that the apparatus of the invention preferably includes a device 21 for measuring one of the desired characteristics (most typically temperature) of the sample 16. Depending upon the nature of the sample 16 and the vessel 15, the parameter measured, particularly temperature, may be that transmitted by the vessel 15 based on its conductive contact with the sample 16. It will be understood, however, that for purposes of the invention, either the vessel temperature or the sample temperature can be usefully measured to control the overall device 10. Where the measuring device 21 is an optical pyrometer and the vessel 15 is transparent infrared radiation, the pyrometer detects the black body radiation from the sample 16 and converts it to the appropriate temperature.

As FIG. 1 further shows, the pyrometer 21 can be connected through appropriate control circuitry schematically designated as the line 22 so that the temperature of the sample 16 as detected by the pyrometer 21 in turn controls the resonant inverter 17 and the magnetron 13 to thereby moderate the microwave radiation 14 sent to the sample 16.

The circuitry 22 that controls the inverter 17 and magnetron 13 in response to the detector 21 can be any appropriate control system, a wide variety of which are known to those of ordinary skill in the art, and can be adapted to the present invention without undue experimentation. Some exemplary descriptions are set forth in Dorf, supra, at page 1104 ("Control Circuits"), page 1255 ("Sensors"), and page 2257 ("Control Systems").

FIG. 2 also schematically illustrates some of the advantages of the invention. FIG. 2 is a top plan of schematic view of a typical microwave device in which the magnetron 13 directs microwave radiation through the waveguide 12 and into the cavity 11 through an opening 23 generally referred to as a "launcher."

In the embodiment shown in FIG. 2, a plurality of reaction vessels 15 are positioned on a turntable 24. The turntable 24 rotates periodically (typically completing a revolution in 7–10 seconds) so that as the microwaves enter the cavity from the launcher, the effects of reinforcement and cancellation of wave energy, and the resulting nodes of energy, are hopefully minimized. As set forth in the background, however, arrangements such as those illustrated in FIG. 2, typically use a single vessel rather than all vessels, to provide feedback on parameters such as temperature and pressure. This is particularly true in closed vessel systems in which obtaining the temperature and pressure within a vessel requires several electrical and physical connections. Because only a single vessel is monitored, the power is turned on or off for all of the vessels based on the single feedback from the controlled vessel. As further set forth above, the net effect of such prior typical arrangement was that power was turned off a lot more frequently than was generally thought with resulting disadvantage to the remainder of the samples in the other vessels.

In contrast, because the invention provides much more controllable power, the problem of using a single reaction vessel for monitoring purposes is greatly reduced. More specifically, the use of lower power levels for longer "on" periods of the duty cycle greatly increases the probability that the microwave power has been applied as uniformly as possible to all of the sample in all of the vessels.

The method and apparatus of the invention are useful in almost any circumstance in which microwave assisted chemistry is useful. This includes techniques, such as drying, digestion, ashing, extraction, chemical synthesis, sintering, or any other related processes.

In the drawings and specification, there have been disclosed typical embodiments of the invention, and, although specific terms have been employed, they have been used in a generic and descriptive sense only and not for purposes of limitation, the scope of the invention being set forth in the following claims.

That which is claimed is:

1. A method of microwave assisted chemistry in which power is supplied in a manner that improves the control and moderation of a chemical reaction, the method comprising:
    measuring the duty cycle required to maintain a measured selected parameter of a sample at a predetermined set point while the sample is being exposed to microwave radiation at a first predetermined power level; and
    moderating the duty cycle and the applied microwave power to increase the on time of the duty cycle while applying power at a second predetermined power level that is sufficient to maintain the sample at the set point using the moderated duty cycle.

2. A method of microwave assisted chemistry according to claim 1 and further comprising:
    applying the first predetermined level of microwave power to the sample until the measured selected parameter reaches the predetermined set point; and
    cycling the power at the first predetermined power level to maintain the sample at the set point;
    both prior to the step of measuring the duty cycle.

3. A method of microwave assisted chemistry according to claim 2 wherein the step of cycling the power comprises switching the power as applied to the sample on and off on a periodic basis.

4. A method according to claim 1 wherein the step of moderating the duty cycle comprises reducing the applied microwave power to a second predetermined level.

5. A method according to claim 1 wherein the step of moderating the duty cycle comprises increasing the applied microwave power to a second predetermined level.

6. A method of microwave assisted chemistry according to claim 1 and further comprising:
    cycling the power at the second predetermined level;
    measuring the duty cycle required to maintain the sample at the set point at the second predetermined power level; and
    further moderating the duty cycle and the applied microwave power to further increase the on time of the duty cycle while applying power at a third predetermined power level that is still sufficient to maintain the sample at the set point using the further moderated duty cycle.

7. A method of microwave assisted chemistry according to claim 6 wherein the step of further moderating the duty cycle comprises reducing the applied microwave power to a third predetermined level.

8. A method of microwave assisted chemistry according to claim 6 wherein the step of further moderating the duty cycle comprises increasing the applied microwave power to a third predetermined level.

9. A method of microwave assisted chemistry according to claim 1 wherein the predetermined set point is selected from the group consisting of: temperature, pressure, gas volume, liquid volume, color, emission, absorption, and electrochemical characteristics.

10. A method of microwave assisted chemistry in which power is supplied in a manner that improves the control and moderation of a chemical reaction, the method comprising:

applying a first predetermined level of microwave power to a sample until the sample reaches a selected temperature;

cycling the power at the first predetermined power level to maintain the sample at the selected temperature;

measuring the duty cycle required to maintain the sample at the selected temperature at the first predetermined power level;

moderating the duty cycle and the applied microwave power to increase the on time of the duty cycle while applying power at a second power level that is sufficient to maintain the sample at the selected temperature using the moderated duty cycle.

11. A method according to claim 10 wherein the step of moderating the duty cycle comprises reducing the applied microwave power to a second predetermined level.

12. A method according to claim 10 wherein the step of moderating the duty cycle comprises increasing the applied microwave power to a second predetermined level.

13. A method of microwave assisted chemistry according to claim 10 and further comprising:

cycling the power at the second predetermined level;

measuring the duty cycle required to maintain the sample at the selected temperature at the second predetermined power level; and further moderating the duty cycle and the applied microwave power to further increase the on time of the duty cycle while applying power at a third predetermined power level that is still sufficient to maintain the sample at the selected temperature using the further moderated duty cycle.

14. A method of microwave assisted chemistry according to claim 13 wherein the step of moderating the duty cycle comprises reducing the applied microwave power to a third predetermined level.

15. A method of microwave assisted chemistry according to claim 13 wherein the step of moderating the duty cycle comprises increasing the applied microwave power to a third predetermined level.

16. A method of microwave assisted chemistry according to claim 10 wherein the step of cycling the power comprises switching the power as applied to the sample on and off on a periodic basis.

17. A method of microwave assisted chemistry comprising driving a magnetron with a variable power supply at a first predetermined power level, directing the microwaves from the magnetron to a sample, measuring a characteristic of the sample while the sample is being exposed to the microwaves, and moderating the output of the variable power supply based upon the measured characteristic, the moderation comprising moderating both the duty cycle and the applied microwave power and applying power at a second predetermined power level that is sufficient to maintain the sample at a set point using the moderated duty cycle.

18. A method of microwave assisted chemistry according to claim 17 wherein the measured characteristic is selected from the group consisting of pressure and temperature.

19. A method of microwave assisted chemistry comprising driving a magnetron with a resonant inverter at a first predetermined power level, directing the microwaves from the magnetron to a sample, measuring a characteristic of the sample while the sample is being exposed to the microwaves, and moderating the output of the resonant inverter based upon the measured characteristic, the moderation comprising moderating both the duty cycle and the applied microwave power and applying power at a second predetermined power level that is sufficient to maintain the sample at a set point using the moderated duty cycle.

20. A method of microwave assisted chemistry according to claim 19 comprising driving the magnetron at relatively high frequency.

21. A method of microwave assisted chemistry in which power is supplied in a manner that improves the control and moderation of a chemical reaction, the method comprising:

applying a first predetermined level of microwave power to a sample until the sample reaches a selected pressure;

cycling the power at the first predetermined power level to maintain the sample at the selected pressure;

measuring the duty cycle required to maintain the sample at the selected pressure at the first predetermined power level; and moderating the duty cycle and the applied microwave power to increase the on time of the duty cycle while applying power at a second power level that is sufficient to maintain the sample at the selected pressure using the moderated duty cycle.

22. A method according to claim 21 wherein the step of moderating the duty cycle comprises reducing the applied microwave power to a second predetermined level.

23. A method according to claim 21 wherein the step of moderating the duty cycle comprises increasing the applied microwave power to a second predetermined level.

24. A method of microwave assisted chemistry according to claim 21 and further comprising:

cycling the power at the second predetermined level;

measuring the duty cycle required to maintain the sample at the selected pressure at the second predetermined power level; and further moderating the duty cycle and the applied microwave power to further increase the on time of the duty cycle while applying power at a third predetermined power level that is still sufficient to maintain the sample at the selected pressure using the further moderated duty cycle.

25. A method of microwave assisted chemistry according to claim 24 wherein the step of moderating the duty cycle comprises reducing the applied microwave power to a third predetermined level.

26. A method of microwave assisted chemistry according to claim 24 wherein the step of moderating the duty cycle comprises increasing the applied microwave power to a third predetermined level.

27. A method of microwave assisted chemistry according to claim 21 wherein the step of cycling the power comprises switching the power as applied to the sample on and off on a periodic basis.

* * * * *